United States Patent [19]

Moore

[11] Patent Number: 4,535,165

[45] Date of Patent: Aug. 13, 1985

[54] SUBSTITUTED DIAZOLES AND THIAZOLES

[75] Inventor: George G. I. Moore, Houlton, Wis.

[73] Assignee: Riker Laboratories, Inc., St. Paul, Minn.

[21] Appl. No.: 552,407

[22] Filed: Nov. 16, 1983

Related U.S. Application Data

[62] Division of Ser. No. 324,063, Nov. 23, 1981.

[51] Int. Cl.$^3$ ............... C07D 277/24; C07D 231/12; C07D 233/64
[52] U.S. Cl. ................................. 548/204; 548/342; 548/378
[58] Field of Search ............... 548/193, 204, 342, 378

[56] References Cited

U.S. PATENT DOCUMENTS

| 4,124,725 | 11/1978 | Moore | 424/330 |
| 4,128,664 | 12/1978 | Moore | 424/324 |
| 4,172,082 | 10/1979 | Moore | 549/72 |
| 4,172,151 | 10/1979 | Moore | 424/330 |

FOREIGN PATENT DOCUMENTS 59090 2/1982 European Pat. Off. .

*Primary Examiner*—Robert Gerstl
*Attorney, Agent, or Firm*—Donald M. Sell; James A. Smith; Robert W. Sprague

[57] ABSTRACT

3,5-di(t-butyl)-4-hydroxyphenyl-substituted pyrazoles, imidazoles, and thiazoles have pharmacological activity as antiinflammatory agents.

5 Claims, No Drawings

SUBSTITUTED DIAZOLES AND THIAZOLES

This is a division of application Ser. No. 324,063 filed Nov. 23, 1981.

TECHNICAL FIELD

This invention relates to certain substituted diazole and thiazole compounds, to the use of such compounds as antiinflammatory agents, and to novel intermediates useful for preparing final product compounds of the invention.

BACKGROUND ART

I have previously synthesized and described several antiinflammatory compounds containing di(t-butyl)-phenol groups. Information regarding these compounds is contained in U.S. Pat. Nos. 4,128,664 (2,6-di(t-butyl)-phenol substituted in the 4-position by an N-substituted carboxamido group), 4,124,725 (2,6-di(t-butyl)phenol substituted in the 4-position by an optionally substituted benzoyl group), 4,172,151 (2,6-di(t-butyl)phenol substituted in the 4-position by an optionally substituted phenyl group), and 4,172,082 (2,6-di(t-butyl)phenol substituted in the 4-position with optionally substituted thiophenyl groups).

DISCLOSURE OF INVENTION

The above described compounds are antiinflammatory agents useful in the treatment of inflammation related conditions such as rheumatoid arthritis. Many of the above compounds also have activity as stabilizers against oxidation, and this characteristic may be related to the efficacy of the above compounds as antiinflammatory agents, although there is no present confirmation of this possibility. The 3,5-di(t-butyl)-4-hydroxyphenyl moiety found in each of the above compounds is also found in the well-known antioxidant 3,5-di(t-butyl)-4-hydroxytoluene (commonly referred to as butylated hydroxytoluene, or "BHT"), a substance which is frequently used as a food additive to extend the shelf life of processed foods. BHT itself has little or no pharmacological value as an antiinflammatory agent. Likewise, many other compounds containing groups derived from di(t-butyl)phenol have little or no pharmacological value, e.g., 2,6-di(t-butyl)phenol, 4-carboxamido-2,6-di(t-butyl)phenol, 4-(2-chlorobenzoyl)-2,6-di(t-butyl)phenol, 4-(5-carboxy-2-thenoyl)-2,6-di(t-butyl)phenol, 2,6-di(t-butyl)-4-phenylsulfonylphenol, 4-acetyl-2,6-di(t-butyl)phenol, and 4-n-octyl-2,6-di(t-butyl)phenol.

Compounds other than those already described in the above-mentioned patents containing 3,5-di(t-butyl)-4-hydroxyphenyl groups may also have pharmacological activity as antiinflammatory agents. However, at the present time there appear to be no rules by which one could correlate structural similarities between various compounds containing the 3,5-di(t-butyl)-4-hydroxyphenyl moiety with the presence of useful antiinflammatory activity in such compounds. New antiinflammatory compounds containing the 3,5-di(t-butyl)-4-hydroxyphenyl moiety must be discovered by trial and error synthesis and testing.

The present invention provides, in one aspect, compounds of the formula:

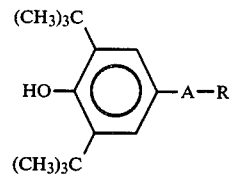

wherein A is a difunctional diazole or thiazole radical selected from the group consisting of pyrazole(1,2-diazole), imidazole(1,3-diazole), and thiazole, and R is a hydrogen atom or a halogen or methyl radical, and pharmaceutically acceptable salts thereof. These compounds have useful antiinflammatory activity. The present invention also provides antiinflammatory compositions containing such compounds, methods for combatting inflammatory reactions in mammals, and novel intermediates useful in preparing such compounds.

DETAILED DESCRIPTION

The compounds of the invention are prepared by the reaction of 2,6-di(t-butyl)benzoquinone with a lithiated diazole or thiazole reagent prepared from an appropriate diazole or thiazole compound corresponding to the diazole or thiazole substituent desired in the final product (Process A). Such lithiated diazole and thiazole reagents are known to the art, as are procedures for their preparation. Among the known lithiated diazoles and thiazoles are lithium 2-(1-methyl)imidazole, lithium 5-(1-methyl)pyrazole, and 2-thiazolyl lithium.

Such reactions between lithiated diazoles or thiazoles and 2,6-di(t-butyl)benzoquinones provide the intermediate optionally substituted 2,6-di(t-butyl)-4-hydroxy-4-azolyl-2,5-cyclohexadien-1-ones having the formula:

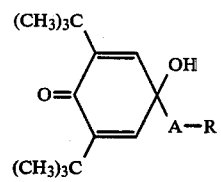

wherein A and R are as defined above for Formula I. These compounds (Formula II) are novel and fall within the scope of the present invention. They are reduced to form compounds of Formula I, using hydrogen gas with a catalyst such as palladium on charcoal or Raney nickel, or by using a metal hydride reducing agent such as lithium aluminum hydride, or by using hydrogen iodide.

The compounds of the invention wherein A is thiazole and R is 2-methyl can be prepared by reaction of 3,5-di(t-butyl)-4-hydroxy-alpha-bromoacetophenone with thioacetamide (Process B). The product is obtained by precipitation, filtration and recrystallization.

Compounds prepared as above can be further reacted using standard methods of organic chemistry, e.g., chlorination or N-alkylation to provide other compounds of Formula I.

Pharmaceutically acceptable salts of the invention (e.g., alkali metal salts and ammonium salts) can be made from compounds of Formula I using methods familiar to those skilled in the art of organic synthesis.

Preferred compounds of the invention are 2,6-di(t-butyl)-4-(1'-methyl-5'-pyrazolyl)phenol, 2,6-di(t-butyl)-4-(1'-methyl-2'-imidazolyl)phenol, 2,6-di(t-butyl)-4-(2'- thiazolyl)phenol, and 2,6-di(t-butyl)-4-(2'-methyl-4'-thiazolyl)phenol, and the preparation of these compounds is described below in Examples 1, 2, 3, and 4, respectively.

In addition to their use as effective antiinflammatory agents, the compounds of the invention are relatively active as stabilizers to prevent oxidation. Some also are analgesics, some are antipyretic agents, and some have mild immunosuppressant activity.

In order to determine and assess pharmacological activity, testing in animals is carried out using various assays known to those skilled in the art. Thus, the antiinflammatory activity of compounds of the invention can be conveniently demonstrated using an assay designed to measure the ability of these compounds to inhibit the enzyme prostaglandin synthetase (cyclooxygenase), such as the test described in White and Glossman, *Prostaglandins*, 7, 123 (1974). The antiinflammatory activity of the compounds of the invention can also be demonstrated using an assay designed to test the ability of these compounds to antagonize the local edema which is characteristic of the inflammatory response (the rat foot edema test). The compounds of the invention are also active when administered dermally. Such topical activity has been measured by means of the guinea pig erythema test and by a contact sensitivity test. Antiinflammatory activity can also be detected by other assays known to the art such as the cotton pellet granuloma test and the adjuvant arthritis test. Analgesic activity has been observed using standard test methods such as the phenylquinone writhing (mouse) and Randall-Selitto (rat) tests.

Leading references to the rat foot edema method are:
(1) Adamkiewicz et al, *Canad. J. Biochem. Physiol.*, 33:332 (1955);
(2) Selye, *Brit. Med. J.*, 2:1129 (1949); and
(3) Winter, *Proc. Exper. Biol. Med.*, 111:544 (1962).

The edema test is performed on adult female rats. Generally, one group of 10 rats serves as non-medicated controls, while another group of 10 rats receives the test compound at various times prior to the induction of the edema, usually 15 minutes, one hour and/or 18 hours. The test compound is administered orally as a suspension in a 4 percent aqueous solution of acacia. Edema is induced by the plantar injection of 0.5 percent carrageenin (0.1 ml/foot) into the right hind foot. The left hind foot receives a like volume of 0.9 percent saline solution. Three hours later, the volume of each hind foot is determined plethysmographically. The edema is expressed as the increase in the volume of the edemogen injected foot less the volume of the saline injected foot. The percent inhibition is calculated by dividing the mean increase in the edema of the medicated group by the mean increase in the edema of the non-medicated group, subtracting this quotient from 1, and multiplying the resulting number by 100. An active dose is that giving a statistically significant inhibition of the induced edema, usually in the range of at least about 25–35 percent inhibition. The preferred compounds of the invention shown in Examples 1, 2, 3, and 4 below exhibit 30 percent, 58 percent, 47 percent, and 47 percent inhibition, respectively, in the above test at doses of 100 mg/kg.

The compounds of the invention preferably are administered orally but other known methods of administration can also be used, e.g., dermatomucosally (for example dermally, rectally and the like), parenterally (for example by subcutaneous injection, intramuscular injection, intraarticular injection, intravenous injection and the like), and by ocular administration. Effective dosages should be less than a toxic amount. Such dosages ordinarily fall within the range of about 1 to 500 mg of the compound of the invention per kg of body weight of the mammal to be treated. Oral dosages are usually below 100 mg/kg. The compounds of the invention ordinarily are administered in the form of compositions containing the compound together with a pharmaceutically acceptable carrier. Suitable compositions for oral administration are in the form of liquids (such as 4 percent acacia and polyethylene glycol solutions), tablets (which can contain anhydrous lactose, microcrystalline cellulose, modified starch, calcium stearate and talc, as well as other conventional compounding agents together with the active antiinflammatory agents), solid suspensions and capsules. Pharmaceutically acceptable carriers for topical application include creams, gels, tapes and the like. Liquid formulations, such as solutions or suspensions of the active ingredient in inert carriers, can be used for dosage by injection.

Using the methods described above, the preparation of compounds of the invention is illustrated in the following examples. The purpose of the examples is to enable those skilled in the art to practice the invention, and they are not intended to limit in any way the scope of the invention.

EXAMPLE 1

Preparation of a Compound of the Invention Using Process A

Step 1

To a chilled (−20° C.) solution of 19.1 g (0.232 mole) of N-methylpyrazole in 300 ml of tetrahydrofuran was added 97 ml (0.233 mole) of n-butyl lithium solution. After stirring for 30 minutes at −5° C., a solution of 51 g (0.233 mole) of 2,6-di(t-butyl)-p-benzoquinone in tetrahydrofuran was added to the reaction mixture while maintaining the temperature of the reaction mixture below 10° C. After stirring the reaction mixture for 16 hours, excess ammonium chloride solution was added to the reaction mixture to effect hydrolysis. Dichloromethane was added to the reaction mixture, followed by separation and drying of the organic layer. Evaporation of the dried organic layer provided a residue which was washed with petroleum ether. The resulting product was 2,6-di(t-butyl)-4-hydroxy-4-(1'-methyl-5'-pyrazolyl)-2,5-cyclohexadiene-1-one, in the form of a tan solid. The structure was confirmed by infrared and nuclear magnetic resonance spectral analysis.

Step 2

A solution of 26 g of 2,6-di(t-butyl)-4-hydroxy-4-(1'-methyl-5'-pyrazolyl)-2,5-cyclohexadien-1-one in 250 ml of ethanol was reduced with hydrogen gas on a Paar apparatus with 10 percent palladium on charcoal as catalyst. After 4 days of reduction the solution was filtered, then evaporated to provide a residue. The residue was washed with hexane and recrystallized from a hexane-benzene mixture to provide a first crop of crystalline material. The first crop was again recrystallized from hexane-benzene to yield white crystals of 2,6-di(t-butyl)-4-(1'-methyl-5'-pyrazolyl)phenol, m.p. 152.5°–154° C.

| Analysis: | % C | % H | % N |
|---|---|---|---|
| Calculated for C$_{18}$H$_{26}$N$_2$O: | 75.5 | 9.1 | 9.8 |
| Found: | 75.8 | 9.2 | 9.8 |

EXAMPLE 2

Preparation of a Compound of the Invention Using Process A

Step 1

To a chilled (−70° C.) solution of 24.6 g (0.30 mole) of N-methylimidazole in tetrahydrofuran was added 125 ml of 2.4M n-butyl lithium in hexane. To this solution was added slowly 66.1 g (0.30 mole) of 2,6-di(t-butyl)-p-benzoquinone while maintaining the temperature below −60° C. The stirred mixture was then allowed to warm to 25° C. under a nitrogen atmosphere and stirred for 16 hours. To the warmed, stirred mixture was added 200 ml of ten percent hydrochloric acid solution. The aqueous layer was separated, basified with fifty percent sodium hydroxide solution to pH 6 and extracted with dichloromethane. The dichloromethane extracts were combined with the tetrahydrofuran layer, dried, and evaporated to yield a residue. The residue was recrystallized from a benzene-hexane mixture to provide off-white crystals of 2,6-di(t-butyl)-4-hydroxy-4-(1'-methyl-2'-imidazolyl)-2,5-cyclohexadien-1-one hydrochloride. The structure was confirmed by infrared and nuclear magnetic resonance spectral analysis.

Step 2

A solution of 20 g of 2,6-di(t-butyl)-4-hydroxy-4-(1'-methyl-2'-imidazolyl)-2,5-cyclohexadien-1-one hydrochloride in 200 ml of ethanol was reduced with hydrogen gas on a Paar apparatus with ten percent palladium on charcoal as catalyst. The theoretical uptake of hydrogen is 5.8 lb, and the observed uptake was 6.0 lb.

The reaction mixture was filtered, then evaporated. The residue was washed with a benzene-hexane mixture, washed with heptane, and recrystallized twice from a dichloroethane-hexane mixture. The product was 2,6-di(t-butyl)-4-(1'-methyl-2'-imidazolyl)phenol hydrochloride, in the form of white crystals, m.p. 260°–263° C. This salt can be converted to the free base by stirring with a dilute aqueous solution of a base such as sodium hydroxide, sodium carbonate, and the like.

| Analysis: | % C | % H | % N |
|---|---|---|---|
| Calculated for C$_{18}$H$_{27}$ClN$_2$ | 67.1 | 8.4 | 8.7 |
| Found: | 66.7 | 8.4 | 8.6 |

EXAMPLE 3

Preparation of a Compound of the Invention Using Process A

Step 1

To a chilled (−70° C.) solution of 8.2 g (0.050 mole) of 2-bromothiazole in 100 ml of diethyl ether was added slowly 20.8 ml of 2.4M n-butyl lithium in diethyl ether while maintaining the temperature below −60° C. After the addition was complete, the solution was stirred for 15 minutes. A solution of 11 g (0.05 mole) of 2,6-di(t-butyl)-p-benzoquinone in ether was added to the reaction mixture while maintaining the temperature of the reaction mixture below −55° C. The reaction mixture was placed under a nitrogen atmosphere, allowed to warm to 25° C., and stirred for 72 hours. The reaction mixture was then poured into 100 ml of ten percent hydrochloric acid and extracted with dichloromethane. The extracts were dried, then evaporated to provide a solid residue which was washed with hexane to provide 2,6-di(t-butyl)-4-hydroxy-4-(2'-thiazolyl)-2,5-cyclohexadien-1-one, in the form of a white solid. The structure was confirmed by infrared and nuclear magnetic resonance spectral analysis.

Step 2

A solution of 10.0 g of 2,6-di(t-butyl)-4-hydroxy-4-(2'-thiazolyl)-2,5-cyclohexadien-1-one in 150 ml of ethanol was reduced with hydrogen gas on a Paar apparatus with ten percent palladium on charcoal as the catalyst. After 12 days of reduction, the mixture was filtered, then evaporated to provide a residue which was recrystallized from hexane and treated with decolorizing charcoal. The product was pinkish-white 2,6-di(t-butyl)-4-(2'-thiazolyl)phenol, m.p. 125°–126.5° C.

| Analysis: | % C | % H | % N |
|---|---|---|---|
| Calculated for C$_{17}$H$_{23}$NOS: | 70.5 | 8.0 | 4.8 |
| Found: | 71.1 | 8.2 | 4.7 |

EXAMPLE 4

Preparation of a Compound of the Invention Using Process B

A mixture of 6.5 g (0.020 mole) of 3,5-di(t-butyl)-4-hydroxy-alpha-bromoacetophenone and 1.5 g (0.020 mole) of thioacetamide in 100 ml of ethanol was heated on a steam bath for one hour. The mixture was diluted with water until it became cloudy, then chilled, yielding a precipitate. The precipitate was separated by filtration, recrystallized from aqueous ethanol, and sublimed at 90° C./0.1 mm Hg. The sublimed material was recrystallized from hexane to provide 2,6-di(t-butyl)-4-(2'-methyl-4'-thiazolyl)phenol in the form of an off-white solid, m.p. 125°–128° C.

| Analysis: | % C | % H | % N |
|---|---|---|---|
| Calculated for C$_{18}$H$_{25}$NOS: | 71.3 | 8.3 | 4.6 |
| Found: | 71.5 | 8.5 | 4.5 |

Various modifications and alterations of this invention will be apparent to those skilled in the art without departing from the scope and spirit of this invention and the latter should not be restricted to that set forth herein for illustrative purposes.

What is claimed is:

1. A compound of the formula

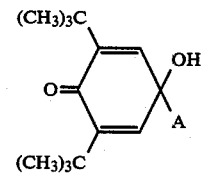

wherein A is a monofunctional diazole or thiazole radical selected from the group consisting of a 1-N-methylpyrazole radical which is bonded to the cyclohexadien- 1-one ring via a carbon atom which is alpha to a nitrogen atom of the pyrazole ring, a 1-N-methylimidazole radical which is bonded to the cyclohexadien-1-one ring via a carbon atom which is alpha to a nitrogen atom of the imidazole ring, and a thiazole radical which may be optionally substituted by a single halogen or methyl radical.

2. The compound 2,6-di(t-butyl)-4-hydroxy-4-(1'-methyl-5'-pyrazolyl)-2,5-cyclohexadiene-1-one.

3. The compound 2,6-di(t-butyl)-4-hydroxy-4-(1'-methyl-2'-imidazolyl)-2,5-cyclohexadien-1-one according to claim 1.

4. The compound 2,6-di(t-butyl)-4-hydroxy-4-(2'-thiazolyl)-2,5-cyclohexadien-1-one according to claim 1.

5. A compound according to claim 1 wherein A is a thiazole radical.

* * * * *